United States Patent
Li et al.

(10) Patent No.: US 9,061,464 B2
(45) Date of Patent: Jun. 23, 2015

(54) RE-ROLLABLE WRAPPING IMPLANT

(75) Inventors: Shu-Tung Li, Oakland, NJ (US); Debbie Yuen, Woodcliff Lake, NJ (US)

(73) Assignee: Collagen Matrix, Inc., Franklin Lakes, NJ (US)

( * ) Notice: Subject to any disclaimer, the term of this patent is extended or adjusted under 35 U.S.C. 154(b) by 872 days.

(21) Appl. No.: 12/203,484

(22) Filed: Sep. 3, 2008

(65) Prior Publication Data
US 2010/0055149 A1    Mar. 4, 2010

(51) Int. Cl.
| | | |
|---|---|---|
| *B29C 53/12* | (2006.01) | |
| *A61F 2/04* | (2013.01) | |
| *B29C 53/32* | (2006.01) | |
| *A61B 19/00* | (2006.01) | |
| *A61F 2/92* | (2013.01) | |
| *B29L 31/00* | (2006.01) | |

(52) U.S. Cl.
CPC ......... *B29C 53/32* (2013.01); *A61B 2019/4884* (2013.01); *A61F 2/04* (2013.01); *A61F 2/92* (2013.01); *B29C 53/12* (2013.01); *B29C 2793/00* (2013.01); *B29L 2031/753* (2013.01)

(58) Field of Classification Search
None
See application file for complete search history.

(56) References Cited

U.S. PATENT DOCUMENTS

| | | | |
|---|---|---|---|
| 4,778,467 A * | 10/1988 | Stensaas et al. ........... 623/23.64 | |
| 4,963,146 A | 10/1990 | Li | |
| 5,026,381 A | 6/1991 | Li | |
| 5,100,429 A | 3/1992 | Sinofsky et al. | |
| 5,376,376 A | 12/1994 | Li | |
| 6,090,996 A * | 7/2000 | Li ............................... 623/23.64 |
| 6,391,333 B1 * | 5/2002 | Li et al. ........................ 424/443 |
| 2003/0028204 A1 | 2/2003 | Li et al. | |
| 2004/0001877 A1 | 1/2004 | Li et al. | |
| 2006/0088578 A1 | 4/2006 | Li et al. | |

OTHER PUBLICATIONS

Neura Wrap Nerve Protector, The Latest Innovation in Peripheral Nerve Protection. INTEGRA, Nov. 2005.
Yuen et al., "Prediction of In Vivo Stability of a Resorbable, Reconstituted Type I Collagen Membrane by In Vivo Methods" *Society for Biomaterials*, p. 222 (2000).
Kline et al., "The Use of a Resorbable Wrapper for Peripheral-Nerve Repair," *Journal of Neurosurgery*, vol. XXI, No. 9, pp. 737-750 (1964).

* cited by examiner

*Primary Examiner* — Scott Long
*Assistant Examiner* — Lyndsey Beckhardt
(74) *Attorney, Agent, or Firm* — Cesari and McKenna, LLP

(57) ABSTRACT

A re-rollable membrane for wrapping around and protecting a cylindrical tissue having an injury site. The membrane includes a sheet of a porous matrix formed of cross-linked biopolymeric fibers. In one implementation, the sheet can be spirally rolled so that at least one portion overlaps another portion of the sheet and, upon absorption of a fluid, the overlapping portions adhere to each other closely so as to exclude penetration of cells. In another implementation, the sheet can be helically rolled to form a helix having a pitch of 2 mm to 40 mm and an inner diameter of 1 mm to 50 mm. Also disclosed are methods for making and using such re-rollable membranes.

8 Claims, 2 Drawing Sheets

RE-ROLLABLE WRAPPING IMPLANT

BACKGROUND

An injury to a tissue and an organ often induces fibrotic scar tissue formation, impeding the function of the healed tissue or organ.

For example, when nerve tissue (e.g., a peripheral nerve such as the median nerve of the wrist) is damaged, scar tissue often forms in and around the injury site, which not only affects nerve signal transmittance and axonal growth across the injury site, but also develops painful neuroma. Similarly, scar tissue formation caused by an injury to a tendon can result tendon adhesion to the surrounding tissue, which, if the tissue is in the joint region, can lead to immobilization of the joint. In addition, a tendon injury may also induce adhesion between the tendon and an adjacent nerve, resulting in severe pain and loss of productivity.

To minimize scar tissue formation within and around an injury site, a biocompatible, semi-permeable, and cell occlusive protective sheet is needed to wrap around the injury site to prevent invasion of fibrogenic cells.

SUMMARY

This invention relates to a re-rollable membrane for wrapping and protecting an injury site, e.g., a damaged nerve.

In one aspect, this invention features a membrane for wrapping around and protecting a cylindrical tissue having an injury site. The membrane includes a sheet of a porous matrix formed of cross-linked biopolymeric fibers, the sheet being spirally rolled so that at least one portion overlaps another portion of the sheet and, upon absorption of a fluid, the overlapping portions closely adhere to each other so as to prohibit cell penetration. The sheet is re-rollable, resorbable, semipermeable, and cell-occlusive; and the sheet has a thickness of 0.05 mm to 1 mm, a density of 0.05 $g/cm^3$ to 0.8 $g/cm^3$, a permeability to molecules having molecular weights no greater than $2\times10^6$ Daltons, a suture pullout strength of 0.1 kg to 1 kg, a re-roll time of 0.1 second to 5 seconds, and an in vivo resorption time of 2 months to 12 months.

The term "cylindrical tissue" used herein refers to both a tissue and an organ that has a cylindrical or tubular shape. Examples include but are not limited to nerve, tendon, blood vessel, ureter, and intestine.

The biopolymeric fibers used to prepare the membrane sheet can be natural polymers, such as collagen, elastin, fibrin, and polysaccharides (e.g., alginic acid, chitosan); synthetic polymers, such as polyglycolic acid, polylactic acid, and polyglycolic-polylactic acid copolymers; genetically engineered materials, or a combination thereof. They can be oriented, i.e., at least half of the fibers in the sheet are in one general direction as determined by the method described in U.S. Pat. No. 6,391,333 or by an analogous method.

The membrane sheet can have a thickness of 0.1 mm to 0.4 mm (e.g., 0.1 mm to 0.3 mm), a density of 0.2 $g/cm^3$ to 0.8 $g/cm^3$ (e.g., 0.2 $g/cm^3$ to 0.5 $g/cm^3$), a permeability to molecules having molecular weights no greater than $1\times10^5$ Daltons (e.g., not greater than $7\times10^4$ Daltons), a suture pullout strength of 0.1 kg to 0.7 kg (e.g., 200 grams to 600 grams), a re-roll time of 0.1 second to 1 second, and an in vivo resorption time of 4 months to 9 months. The height of the sheet ("H," i.e., the dimension along the longitudinal direction) can range from 1 cm to 10 cm (e.g., from 2 cm to 5 cm). The length of the sheet ("L," i.e., the dimension along the circumferential direction) can range from 0.4 cm to 20 cm (e.g., from 0.4 cm to 4 cm). The length can be predetermined based on the circumference of the cylindrical tissue having the injury site. Preferably, the length is less then twice the circumference of said tissue. More preferably, the length is about 1.2 to 1.5 times of the circumference of said tissue.

A bioactive agent can be included in the membrane of this invention to promote wound healing and/or to prevent tissue adhesion. Examples include but are not limited to growth factors, cytokines, laminins, glycosaminoglycans, glycoproteins, fibronectins, drugs (e.g., rapamycin, antibiotics) and the like. The bioactive agent may be incorporated into the membrane via electrostatic interactions, physical or mechanical interactions, covalent bonding using crosslinking agents or light, a combination of the above, or via a spacer molecule that is well known in the art.

In another aspect, this invention features a membrane for wrapping around and protecting a cylindrical tissue having an injury site. The membrane includes a sheet of a porous matrix formed of cross-linked biopolymeric fibers, the sheet being helically rolled to form a helix having a pitch of 2 mm to 40 mm and an inner diameter of 1 mm to 50 mm.

The pitch ("p") used herein is the shortest distance between two neighboring helix repeating units. As will be demonstrated below, the pitch of a helically-rolled sheet is the sum of the width ("w") of the sheet and the gap ("g") between the two neighboring helix units.

The helically-rolled membrane sheet can be re-rollable, resorbable, semipermeable, and cell-occlusive. It can have a thickness of 0.05 mm to 1 mm (e.g., 0.1 mm to 0.4 mm), a density of 0.05 $g/cm^3$ to 0.8 $g/cm^3$ (e.g., 0.2 $g/cm^3$ to 0.8 $g/cm^3$), a width of 2 mm to 30 mm, a permeability to molecules having molecular weights no greater than $2\times10^6$ Daltons (e.g., not greater than $1\times10^5$ Daltons, or not greater than $7\times10^4$ Daltons), a suture pullout strength of 0.1 kg to 1 kg (e.g., 0.1 kg to 0.5 kg), a re-roll time of 0.1 second to 5 seconds (e.g., 0.1 second to 1 second), and an in vivo resorption time of 2 months to 12 months (e.g., 4 to 9 months). The height of the helically-rolled sheet ("h") can range from 1 cm to 10 cm. The biopolymeric fibers used to prepare the helical membrane sheet may be oriented and/or collagen fibers.

As well recognized by one skilled in the art, the measurements of the thickness, density, height, length, pitch, diameter, width, and gap between two neighboring units of the membrane sheet set forth herein are determined in a dry state; on the other hand, measurements of the permeability, suture pullout strength, re-roll time, and in vivo resorption time of the sheet set forth herein are determined in a hydrated state or upon absorption of a fluid. Drying the membrane sheet can be easily achieved by air drying in a hood overnight, or by any other methods, e.g., freeze-drying, which bring about the same or similar state of dryness. Different drying methods or conditions can be applied to selectively control the effective pore size of the membrane sheet, as will be described in more detail below. As used herein, the term "effective pore size" refers to the maximum diameter of a molecule, which can pass through a pore in the membrane sheet. A molecule's molecular weight is typically related to its size and thus corresponds to a specific effective pore size of the membrane sheet. For example, a membrane sheet that is permeable to molecules with a molecular weight of no greater than $1\times10^5$ Dalton has an effective pore size of 5 nanometers (nm). Preferably, the sheet has an effective pore size ranging from 1 nm to 4 micron (e.g., from 1 nm to 4 nm).

In still another aspect, this invention relates to a method of preparing a spirally-rolled membrane. The method includes reconstituting biopolymeric fibers dispersed in a solution; placing the reconstituted biopolymeric fibers around a first mandrel; rotating the first mandrel to convert the reconstituted biopolymeric fibers on the mandrel into a tubular membrane; drying the tubular membrane; cutting the tubular membrane longitudinally; rolling the cut membrane longitudinally onto a second mandrel having a smaller diameter than the first mandrel so that at least one portion of the membrane overlaps another portion of the membrane; inserting the rolled membrane into a tubular mesh; and cross-linking the biopolymeric fibers, thereby forming a spirally-rolled membrane of oriented biopolymeric fibers. The biopolymeric fibers preferably are collagen fibers.

In yet another aspect, this invention relates to a method of preparing a helically-rolled membrane. The method includes reconstituting biopolymeric fibers dispersed in a solution; placing the reconstituted biopolymeric fibers around a mandrel; rotating the mandrel to convert the reconstituted biopolymeric fibers on the mandrel into a tubular membrane; drying the tubular membrane; removing the membrane from the mandrel; cross-linking the biopolymeric fibers; inserting the membrane into a cutting guidance mold; and cutting the membrane, thereby forming a helically-rolled membrane of oriented biopolymeric fibers, having a pitch of 2 mm to 40 mm and a width of 2 mm to 30 mm. The biopolymeric fibers preferably are collagen fibers.

Also within the scope of this invention are a spirally-rolled membrane and a helically-rolled membrane prepared by the above-described methods respectively.

Further, this invention relates to a method for wrapping around and protecting a cylindrical tissue having an injury site. The method includes placing a spirally-rolled membrane or a helically-rolled membrane of the invention in a fluid to allow the membrane to hydrate; unrolling the hydrated membrane with a force; and bringing the unrolled membrane within the proximity of the injury site, so that, upon release of the force, the membrane re-rolls and wraps the injury site.

Aspects can include one or more of the following advantages. The membrane for wrapping an injured cylindrical tissue is bioresorbable and the rate of resorption is balanced with the rate of wound healing of the injured tissue to prevent any complications caused by premature degradation of the membrane, such as scar formation. The membrane is semipermeable. More specifically, the membrane is only permeable to molecules smaller than the effective pore size of the membrane, such as nutrient molecules, which can therefore pass through the membrane to reach the wound site and support wound healing. Meanwhile the membrane is impermeable to large molecules such as fibrogenic cells, which usually invade the wound site to form undesirable scar tissues. The membrane is cell occlusive. As just described, the membrane does not allow infiltration of fibrogenic cells to reach the wound site and induce scar formation. The membrane does not adhere to the repaired tissue. The membrane in its hydrated state can quickly restore its original rolled configuration when released from a force that unrolls the membrane. The re-roll time can be less than 1 second. This re-roll or self-roll feature allows easy application of the membrane to an injured tissue and/or significant reduction of the surgery time. More specifically, upon release of a mechanical unrolling force, the membrane in its hydrated state self-rolls to conform to the cylindrical shape of the tissue or organ with at least two overlaps of the membrane adhering to each other so as to exclude penetration of cells. Due to its self-rolling and conforming characteristics, suturing of the membrane is often not needed. If necessary, for example, if the injured tissue is significantly distorted from its original cylindrical shape, the membrane can be sutured to the surrounding tissue or the epineurial tissue for additional stability. The membrane has sufficient suture pullout strength for stabilizing it with the surrounding tissue. In addition, a helically-rolled membrane may be used to wrap an injured tissue with a distorted cylindrical shape shapes without suturing, as it conforms to an irregular shape more readily than a spirally-rolled membrane. The membrane formed of oriented biopolymeric fibers is more resistant to tearing, due to a higher mechanical strength, than the conventional membrane formed of randomly oriented fibers.

The details of one or more embodiments of the invention are set forth in the description below. Other features, objects, and advantages of the invention will be apparent from the description and drawings, and from the claims.

DETAILED DESCRIPTION

The invention relates to a resorbable, semipermeable, cell occlusive, biocompatible, re-rollable membrane for wrapping and protecting an injured tissue. Such a membrane can be implanted around damaged cylindrical, tubular tissues or organs (e.g., peripheral nerves or tendons) to protect them from scar formation and to assist in wound healing.

Figure 1A:
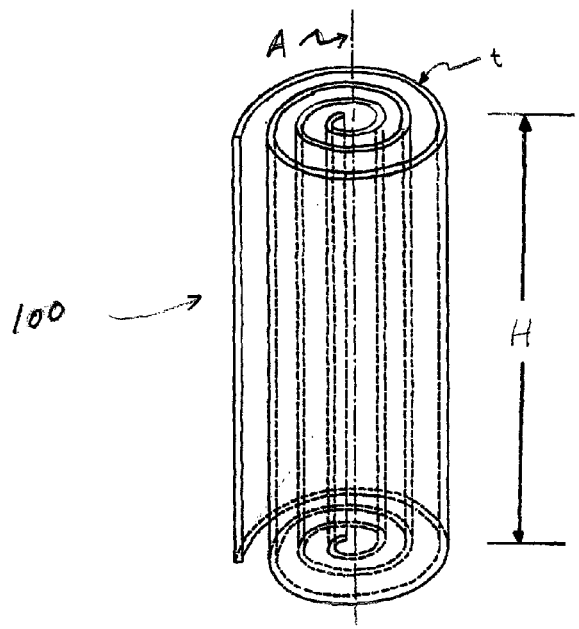
FIG. 1a is a perspective view of a spirally-rolled membrane.
Figure 1B:
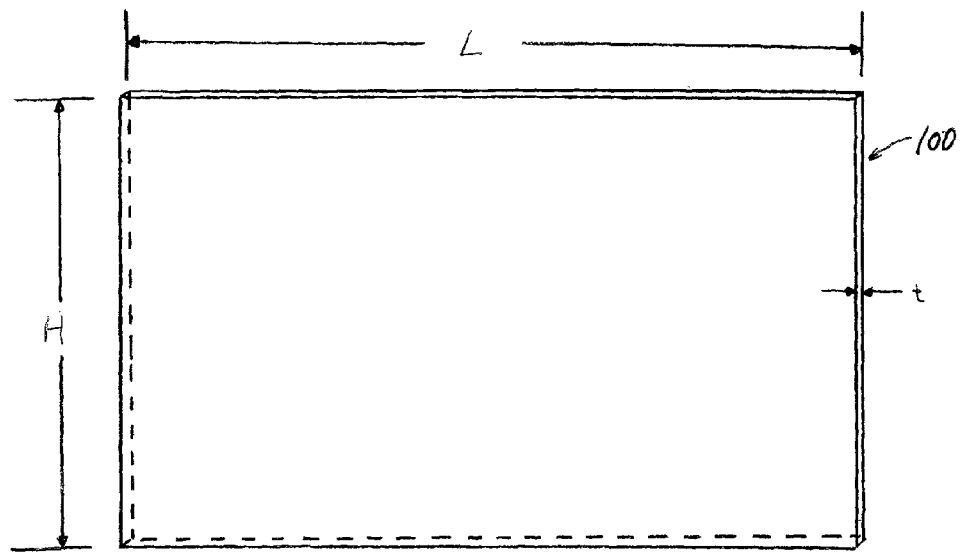
FIG. 1b is a perspective view of the membrane in FIG. 1a in its unrolled configuration.
Figure 2A:
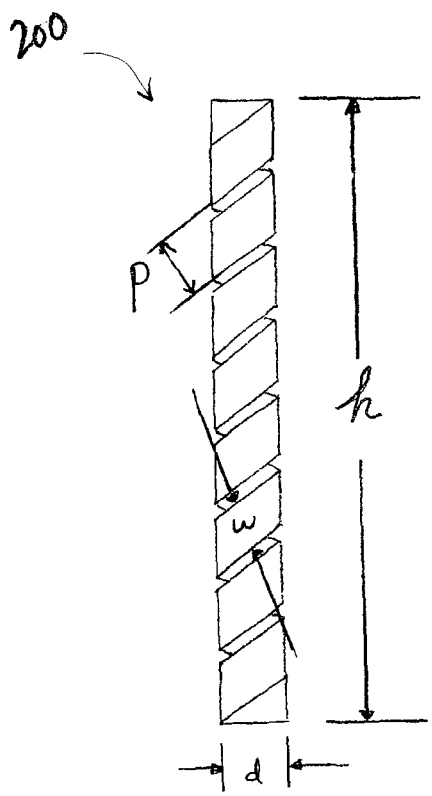
FIG. 2a is perspective view of a helically-rolled membrane.
Figure 2B:
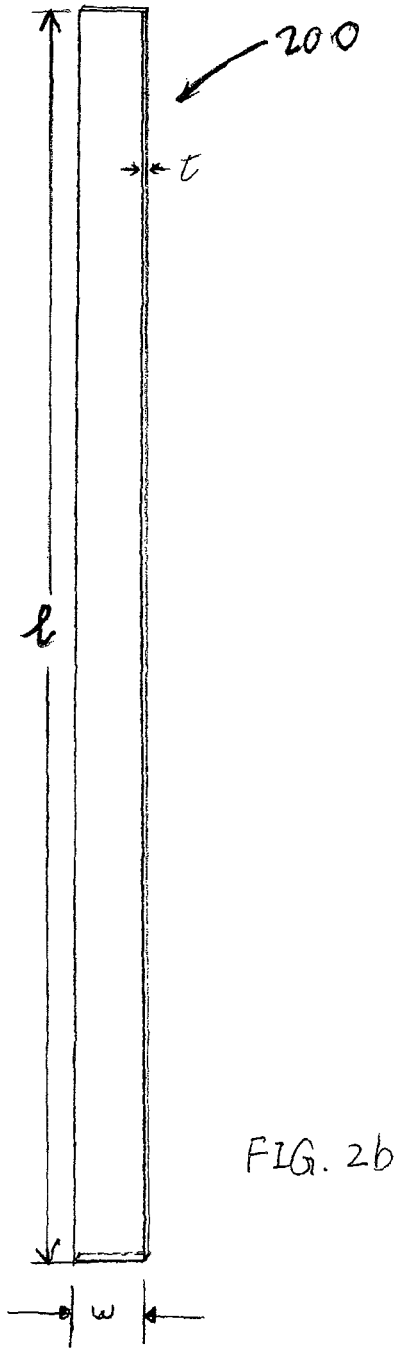
FIG. 2b is a perspective view of the membrane in FIG. 2a in its unrolled configuration.

FIGS. 1a and 2a show two exemplary membranes of this invention, either spirally rolled or helically rolled. Referring particularly to FIG. 1a, the membrane of this invention is a spirally-rolled sheet 100 along its longitudinal axis "A". The sheet has thickness "t" and a height "H." When unrolled by an external force, the sheet has a length "L," as shown in FIG. 1b. Preferably, the length and height of the sheet is sufficient to wrap an injured tissue with a diameter of up to 5 cm and a length of up to 20 cm. However, size greater than that described herein can also be fabricated if needed. Refereeing particularly to FIG. 2a, the membrane of this invention is a helically-rolled sheet 200 with a thickness "t" (shown in FIG. 2b), a height "h," a width "w," a pitch "p," and an inner diameter "d." When unrolled by an external force, the sheet has a length "l," as shown in FIG. 2b.

Type I collagen fibers are the preferred material for preparing the membranes of the present invention due to their biocompatibility and ease in accessing large quantities of the material from animal source. Other biopolymeric materials, which can be natural or synthetic, include but are not limited to, other types of collagen (e.g., type II to type XXI), elastin, fibrin, polysaccharide (e.g., chitosan, alginic acid, cellulose, and glycosaminoglycan), a synthetic analog of a biopolymer by genetic engineering techniques, or a combination thereof.

To fabricate a type I collagen-based membrane, an acid dispersion of type I collagen fibers with a solid content of about 0.5 to 1.0% (w/w) is first prepared. Both inorganic and organic acids can be used. However, organic acids are preferred (e.g., lactic acid). Typically, a 0.05 M to 0.1M lactic acid dispersion of collagen has a pH about 2.3 to 2.5. The dispersed collagen fibers are homogenized using a commercial homogenizer to mechanically disintegrate the fibers into smaller fibrils. After removal of air bubbles by vacuum, the dispersed fibrils are reconstituted into long fibers by adjusting the pH to about 4.7, the isoelectric point of the purified collagen as prepared by methods described in U.S. Pat. No. 6,391,333.

The reconstituted collagen fibers are then preferentially oriented circumferentially onto a rotating mandrel having a defined outer diameter with a rotational speed preferably greater than 50 RPM, and dried (e.g., freeze dried) by methods well known in the art. Depending on the desired permeability properties of the membrane, the drying can either be by air- or freeze-drying. Air-drying produces a membrane which allows the permeation of ions or small peptides (e.g., those having molecular weights less than 2,000), whereas the freeze-dried membranes permit the permeation of molecules with molecular weights ranging from 200 to 2,000,000 (e.g., various peptides, growth factors, and bioactive macromolecules with molecular weights ranging from 200 to 300,000). Desired permeability properties of the membranes can also be obtained by controlling the extent of membrane dehydration prior to freeze-drying.

To fabricate the membrane shown in FIG. 1a, the dried (e.g., freeze-dried) tubular membrane is then removed from the mandrel by cutting open along the longitudinal direction (e.g., axis A) using a scalpel. The cut membrane is then rolled along the same axis onto a second mandrel having a diameter smaller than the original mandrel. As an example, the original mandrel has an outer diameter of 10 mm and the second mandrel has an outer diameter of 5 mm. By rolling the membrane onto a smaller mandrel, a spirally-rolled membrane with overlaps is produced, as illustrated in FIG. 1a.

The rolled membrane is then inserted into a tubular mesh having an inner diameter approximately the size of the outer diameter of the rolled sheet, and crosslinked using a crosslinking agent such as an aldehyde (e.g., formaldehyde vapor) to fix and preserve the configuration. Other crosslinking agents with sufficient vapor pressure can also be used. Unreacted crosslinking agent can be removed via rinsing with water. The rinsed membrane can be dried again before use. The tubular mesh can be made of synthetic polymeric materials or stainless steel.

To fabricate the membrane shown in FIG. 2a, the above-described dried (e.g., freeze-dried) tubular membrane is removed from the mandrel and re-inserted into a cutting mold such as a guiding tube that has a helical cutting guide. The tubular membrane, is then cut along the guide to produce a helically-rolled membrane with a defined pitch (as shown in FIG. 2a) either before or after the crosslinking step described above. The size of the gaps between neighboring units of the membrane can be controlled to range from substantially zero, e.g., 0.001 mm to about 10 mm. Alternatively or additionally, the as-formed helical membrane described above may be unfolded and re-rolled onto a second mandrel having a diameter smaller than the original mandrel. By re-rolling the membrane onto a smaller mandrel, the gaps formed by cutting may be eliminated and/or overlaps between neighboring units may be created.

It is of particular significance to create a spirally-rolled or a helically-rolled membrane of this invention from a tubular membrane rather than from a planar sheet. Without wishing to be bond by theory, the initial rolled configuration of a tubular membrane allows a permanent fixation of the rolled geometry of the membranes of this invention. In addition, when starting with an oriented tubular membrane, the initial orientation of the biopolymeric fibers along the circumferential direction of the tubular membrane further strengthens a permanent fixation of the rolled geometry. On the contrary, a rolled membrane made from a planner sheet will slowly relax to the open unrolled configuration over time. A permanent fixation of the initially rolled geometry permits the re-rolling feature of the membranes of the invention. In particular, the membranes of this invention can automatically restore to a tubular-like geometry by an inward compressive force.

The extent of crosslinking determines the in vivo stability of the membrane. Depending on the functional requirements in vivo, the extent of crosslinking may be controlled accordingly. More specifically, the extent of crosslinking in solution phase may be controlled by crosslinking agent, concentration, temperature, pH, and time of crosslinking. The crosslinking in vapor may be controlled by vapor pressure, temperature, and time of crosslinking. In vivo stability depends on the nature of the crosslinks formed by various crosslinking agents. Generally, glutaraldehyde forms more stable crosslinks than formaldehyde and carbodiimide. Thus, glutaraldehyde has been used to crosslink tissue heart valves for in vivo durability, and formaldehyde has often been used to crosslink resorbable implants.

The extent of crosslinking may be determined by methods well known in the art such as by monitoring the hydrothermal shrinkage temperature. In other words, the hydrothermal shrinkage temperature of a crosslinked membrane is correlated to the in vivo resorption time. For example, using formaldehyde vapor as a crosslinking agent, as described in Yuen et al., *Trans Six World Biomaterials Congress, page* 222 (2000), the hydrothermal shrinkage temperature of the as-formed membrane is in the range from about 48° C. to about 70° C. corresponding to an in vivo resorption time in the range of 2 to 12 months.

Figure 1C:
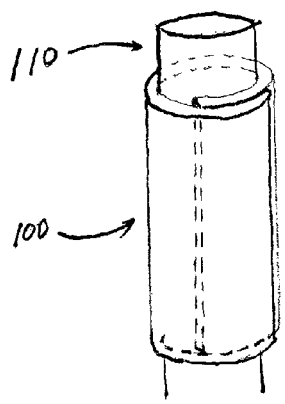
FIG. 1c is a perspective view of the membrane in FIG. 1a when applied to wrap a cylindrical tissue.

The membranes of this invention, as exemplified in FIGS. 1a and 2a can be used to wrap a cylindrical tissue such as a nerve or tendon. Particularly, when using the membrane as shown in FIG. 1a for wrapping an injured tissue, an appropriately sized membrane is first hydrated in an aqueous solution. Preferably, the length "L" of the membrane is about 1.2 to 1.5 times of the circumference of the target tissue and the dimension of the sheet along the longitudinal direction extends at least 0.5 cm beyond each of the ends of the injury site. The hydrated implant is then mechanically un-rolled, e.g., by hand, into an open configuration as shown in FIG. 1b. The opened membrane sheet 100 is then brought close to the injury site, e.g., placed around the injured tissue. Upon release of the external force, the opened membrane sheet automatically recoils and conforms to the shape of the injured tissue, forming a protective sheath, as shown in FIG. 1c (in which the wrapped tissue is labeled with number 110). As also illustrated in FIG. 1c, the overlaps of the membrane 100 adhere closely to each other such that the membrane can be left in situ without suturing. If necessary, the membrane may be sutured to the surrounding tissue or to the epineurium tissue for stability. Similarly, when applying the membrane shown in FIG. 2a to an injured tissue, the membrane of an appropriate size (e.g., "d" equivalent to or smaller than the outer diameter of the injured tissue) is first hydrated in an aqueous solution. The hydrated membrane is then un-rolled to an open configuration from one end as shown in FIG. 2b. The opened membrane sheet 200 is then placed around the injured tissue. Upon release of the external force, the opened sheet automatically recoils to its rolled configuration to cover a section of the injured nerve. The opening and self-rolling process described above can be repeated until all of the injury sites of the tissue is wrapped. If necessary, the membrane may be sutured to the surrounding tissue for additional stability. To prevent penetration of fibrogenic cells through the gaps between neighboring units of the helical membrane, the gaps can be closed by suturing.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Preparation of Collagen Fibers

Bovine flexor tendon was cleaned by removing fat and fascia, and washed with water. The cleaned tendon was frozen and comminuted into 0.5 mm slices with a meat slicer. One kilogram of the sliced wet tendon was subsequently extracted with 5 L of distilled water and with 5 L of 0.2 N HCl/0.5 M $Na_2SO_4$ at room temperature for 24 hours, the extracts were discarded. The residual acid on the tendon was removed by washing with 5 L of 0.5M $Na_2SO_4$ solution. The tendon was again extracted with 5 L of 0.75 M NaOH/1.0 M $Na_2SO_4$ solution at room temperature for 24 hours. The extract was also discarded. The residual base was neutralized with a 0.1N HCl solution to pH 5, followed by several washes with distilled water to remove the residual salts on the purified tendon. The tendon was then defatted at 25° C. under constant agitation with isopropanol of 5 times the volume of the tendon for 8 hours and an equal volume of the tendon overnight. The defatted tendon was then air-dried and stored at room temperature until further processing.

Preparation of Collagen Fiber Dispersion

An aliquot of the insoluble purified collagen fibers was weighed and dispersed in 0.07 M lactic acid, homogenized with a Silverson Homogenizer (East Longmeadow, Mass.), and filtered with a 30 mesh stainless steel mesh filter to obtain a dispersion containing 0.7% (w/v) collagen. The dispersion was de-aerated under vacuum to remove the air trapped in the dispersion and stored at 4° C. until use.

Preparation of a Spirally-Rolled Tissue Wrap Implant

The acid dispersed collagen fibers prepared in Example 2 were reconstituted by adding 0.3% $NH_4OH$ to adjust the pH of the dispersion to the isoelectric point of collagen (pH 4.5-5.0). The reconstituted fibers were poured into a fabrication device which was set up with the insertion of a mandrel of 5 mm, 10 mm, 15 mm, 20 mm, or 30 mm in diameter. The fibers were evenly distributed along the mandrel. The mandrel was then slowly rotated at about 50-100 rpm to firmly wind the fibers around it. The fibers on the mandrel were removed from the fabrication device and then inserted into a precision dehydration device for removal of excess solution and control of the thickness and density of the tubular wall. Dehydration of the device resulted in increased wall density of the device and decreased pore size (i.e., the inter-fiber space), thereby controlling the permeability of the wall. The excess solution was removed by compressing the hydrated fibers on the rotating mandrel against two plates that precisely control the thickness of the wall of the membrane.

The partially dehydrated collagen fibers were freeze-dried at −10° C. for 24 hours and at 20° C. for 16 hours under a pressure less than 200 millitorr using a Virtis Freeze Dryer (Gardiner, N.Y.). The freeze-dried tubular matrix was removed from the mandrel and a cut was made along the longitudinal direction of the tube. The opened tube was then rolled around a smaller mandrel forming a rolled sheet. The rolled sheet was inserted into a tubular mesh having a diameter slightly larger than the diameter of the rolled sheet. The rolled sheet matrix was then chemically cross-linked with formaldehyde vapor at the humidity of 90-95% for 3-6 hours to stabilize the sheet in its rolled configuration and to control their in vivo stability. The cross-linked matrix was rinsed in water and air or freeze-dried. An example of the as-formed implant device is shown in FIG. 1a.

Preparation of a Helically-Rolled Tissue Wrap Implant

The acid dispersed collagen fibers prepared in Example 2 were reconstituted by adding 0.3% $NH_4OH$ to adjust the pH of the dispersion to the isoelectric point of collagen (pH 4.5-5.0). The reconstituted fibers were poured into a fabrication device which was set up with the insertion of a mandrel of 5 mm, 10 mm, 15 mm, 20 mm, or 30 mm in diameter. The fibers were evenly distributed along the mandrel. The mandrel was then slowly rotated at about 50-100 rpm to firmly wind the fibers around it. The fibers on the mandrel were removed from the fabrication device and then inserted into a precision dehydration device for removal of excess solution and control of the thickness and density of the tubular wall. Dehydration of the device resulted in increased wall density of the device and decreased pore size (i.e., the inter-fiber space), thereby controlling the permeability of the wall. The excess solution was removed by compressing the hydrated fibers on the rotating mandrel against two plates that precisely control the thickness of the wall of the membrane.

The partially dehydrated collagen fibers were freeze-dried at −10° C. for 24 hours and at 20° C. for 16 hours under a pressure less than 200 millitorr using a Virtis Freeze Dryer (Gardiner, N.Y.). The freeze-dried tubular matrix was removed from the mandrel and the tubular membrane was then chemically cross-linked with formaldehyde vapor at the humidity of 90-95% for 3-6 hours to stabilize the tubular configuration and to control their in vivo stability. The cross-linked matrix was rinsed in water and air or freeze-dried. The dried tubular membrane was then inserted into a cutting guide. The membrane was cut along the guide line to produce a helically-rolled sheet ribbon. An example of the as-formed implant device is shown in FIG. 2a.

Characterization of Tissue Wrap Implants

Physicochemical and mechanical characteristics of tissue wrap implants prepared in Examples 3 and 4 were assessed in the following aspects:

i) Hydrothermal Shrinkage Temperature

The hydrothermal shrinkage temperature ($T_s$) was determined by a measurement of the thermal transition temperature of the hydrated collagen matrix. A sample was first cut into a 0.25 mm diameter and then placed in an aluminum pan. The sample was then hydrated with 15 µl of phosphate buffer saline and the pan sealed. $T_s$ was determined using a Mettler Toledo differential scanning calorimeter (DSC) at a heat rate of 5° C. per minute. The thermal transition temperature is defined as the onset temperature by extrapolation to the baseline of most rapid rise in the excess heat capacity as a function of temperature curve.

ii) In Vivo Stability Evaluation

The in vivo stability and resorbability of a tissue wrap implant membrane was determined by the following experiment: Collagen membrane materials with different hydrothermal shrinkage temperatures were implanted subcutaneously in rats. At predetermined time points the rats were sacrificed and the amount of residual collagen implants remaining was determined by histological means. The total resorption time of each membrane material was obtained by extrapolation of the residual amount of collagen as a function of time to a value where the area occupied by the residual implant collagen was less than 2%. The total resorption time and the hydrothermal shrinkage temperature of the membranes has a linear relationship (Yuen, et al., Trans Soc. Biomaterials, 2000)

Based on the relationship, a membrane matrix material can be selected for certain in vivo stability, based on its hydrothermal shrinkage temperature. For example, if the desired in vivo stability is 4-6 months, a hydrothermal shrinkage temperature of the tissue wrap implant in the range 50-55° C. will be suitable.

iii) Apparent Density

The apparent density of a dry tissue wrap implant was determined by a gravimetric method. The implant was first dried under vacuum for 24 hours and the dry weight was recorded. The dimensions (length, thickness and width) of the implant were then measured with a micrometer. Thus, the density was a measure of the amount of collagen per unit volume of implant and was represented in $g/cm^3$.

iv) Suture Pullout Strength

Suture pullout strength was determined as follows: The implant was cut to a size of 20 mm×5 mm and soaked in pH 7.4 PBS at 25° C. for about 5 minutes. A suture (3-0 silk black braided, taper SH-1, Ethicon, Somerville, N.J.) was placed through the 20 mm membrane side at approximately 3 mm from the edge. The suture was tied into a knot, secured to the hook adapter of the tensile tester, clamped, and pulled at a speed of 2.54 cm/minute until the suture was pulled out and pull-out strength recorded.

v) Recovery of the Rolled Geometry from a Mechanically Distorted Configuration

A hydrated tissue wrap implant was mechanically distorted from its rolled geometry to open sheet geometry. The external force was then released and the time required from the open geometry to the rolled geometry was recorded.

vi) Permeability

A 2-cm diameter disk cut from a membrane of this invention was inserted into a two compartment chamber containing phosphate buffered saline (PBS). A fixed volume of PBS containing 50 μg of various sizes of peptide and protein molecules per mL was added to one compartment. The solution in both compartments was allowed to equilibrate for 24 hours. A calorimetric assay was then conducted to determine the amount of peptide or protein molecules in the compartment which initially only contained PBS.

The results of the characterization studies are summarized in Table 1.

TABLE 1

| | |
|---|---|
| Hydrothermal Shrinkage Temperature (° C.) | 51.4 ± 0.6 |
| In vivo stability (month) | 4-5 |
| Apparent Density (g/cm$^3$) | 0.43 ± 0.07 |
| Suture Pull-out Strength | 246 ± 24 |
| Inward re-rolling time (second) | <1 |
| Permeability to carbonic anhydrase MW = 29,000 (%) | 4.2 ± 0.9 |

In Vitro and in Vivo Evaluations i) In Vitro Cell Culture Study:

3T3 fibroblasts (ATCC) were cultured (2×10$^6$ cells in 200 μl) on the top of the tissue wrap membrane. Each membrane was cut to 1 cm circles to fit in Millipore Millicell inserts in a 24-well cell culture plate. Each Millicell was pre-wet as per package instructions and each membrane was incubated in medium for 24 hours in the insert prior to cell seeding. Harvest was at 24 hours and 48 hours in duplicate. The membranes in the Millicell were cut circumferentially and left attached to the membrane matrices. After formalin fixation, each matrix was cut through the center and both cut sides embedded with H&E to show cells. Slides were examined by light microscopy and results photographed.

Results of the in vitro study showed that 3T3 fibroblasts grew only on surface of the membrane matrix. By 48 hours incubation, the cell layers had detached from the matrix whether the cells were seeded on either side of surface. This indicated that the tissue wrap membrane was unexpectedly impermeable to cells and might have an inherent non-adherent property. This observation is consistent with cell occlusive structure of tissue wrap membrane.

ii) In Vivo Implantation Study:

The tissue wrap membrane was implanted as a dura substitute in a rabbit model to evaluate the potential adhesion of the membrane to the surrounding tissue and the resorption and new tissue growth characteristics. New Zealand White male rabbits (3-4 kg) were sedated with 0.5 cc/kg "rabbit mix" (Ketamine: 5 cc of 100 mg/mL, Xylazine: 8 cc of 20 mg/mL, Acepromazine: 2 cc of 100 mg/mL), intramuscularly and maintained with isoflurane (5% isoflurane, 3% oxygen) via endotracheal tube. Animals were placed on a heating pad, and attached to EKG leads. Scalps were shaved and washed with Betadine. Under aseptic conditions, a midline incision was made over the scalp with a number 11 scalpel blade and the calvarium was exposed using a periosteal elevator. The area immediately anterior to the coronal suture on the right lateral aspect of the calvarium was marked and a Dremel tool fitted with a 1 mm burr was used to carefully drill out an oval section of the overlying bone exposing the dura. A small rongeur was used to remove the last bone fragments and with a small spatula the bone was separated from the dura and removed and placed in saline. The defect was cleaned with saline and gauze, inspected and bone fragments removed. Holes (2-3) were drilled in the bone flap and the adjacent area of the calvarium for later attachment of the bone flap. Using 7-0 suture (Deknatel) with a ⅜ inch needle the dura was hooked and lifted from the brain. A small iris scissor was used to open an 8 mm×8 mm square defect in the dura.

Tissue wrap membrane was soaked in sterile saline for 5 minutes and tailored to fit the site and placed over the dural defect with an approximate 3 mm overlap of the native dura in an onlay fashion, and not sutured in place.

In vivo implantation of the wrap membrane exhibited very little adhesion to bone (score 1.25) compared to normal (2.0) at 12 weeks post implantation time. Implants were clearly visible and well integrated at the periphery of the native dura. Unexpectedly, there was no adhesion to the cortex of the brain (score 0.0). The implant and native dura appeared continuous, with the implant/regenerate similar in appearance to native dura. The results indicated that this implant provided a protective covering of the cortex and was biocompatible as it integrated with the native dura and may have promoted regeneration of dura.

When the implants were removed from the surgical sites and pulled between two pair of forceps, tissue wrap membrane had similar strength as the normal dura (score 2.0 for normal vs. 2.8 for wrap membrane). Strength rankings were made visually as each implant was pulled apart to obtain relative strength of each implant semi-quantitatively.

The resorption and regeneration was estimated based on the amount of implant collagen degradation and the deposition of newly synthesized collagen deposition. A semi-quantitative estimation of the rate of resorption and rate of new tissue regeneration of the tissue wrap implants based on histological analysis and the gross observation showed that tissue wrap membrane had a balanced rate of resorption and rate of new tissue regeneration. At any time point during the course of the experiment the total amount of collagen was maintained. The newly deposited collagen did not cause any adhesion problem, suggesting that the tissue was functional rather than the fibrotic or scar like tissue that often occurred as a result of inflammation reaction or foreign body reaction towards the implant. In addition, the implant-new tissue complex had a resistance to pull, i.e., it has a relatively high mechanical strength.

In Vivo Evaluation of a Spirally-Rolled Tendon Wrap Implant as a Protective Sheet for Tendon Repair A total of 7 adult male New Zealand White rabbits (4.0-4.5 kg) were used in the study. Twenty digits from forepaws underwent tendon repair surgery. Anesthesia for all procedures consisted of an induction with combined ketamine, medetomidine, butorphanol intramuscular injection, followed by maintenance of general anesthesia using isoflurane. All surgeries were performed using aseptic techniques.

Following general anesthesia, right or both forepaws of the rabbit were shaved and prepared with betadine solution. The flexor surfaces of the second and forth digits of the forepaws were incised over the basal and middle phalanges. With sharp dissection, the flexor tendon sheaths of the digits were identified and opened by an anterolateral incision. The flexor digitorum profundus tendons were identified between the first and second annular pulleys, lifted from between the slips of the flexor digitorum superficialis, and divided transversely with a sharp scalpel. The tendon was then repaired by 7-0 nonabsorbable monofilament suture.

The animals were divided into three groups. In Group 1 (n=7 digits), a spirally-rolled tendon wrap, 1 cm in length (i.e., the height H in FIG. 1a), was wrapped circumferentially around the repaired tendon in place of its damaged sheath and the ends of the wrap were sutured to each other with 8-0 nylon. In Group 2 (n=6 digits), no tendon protector sheet was applied after tendon repair, as the control. In Group 3 (n=7 digits), the tendon was not divided or repaired, as the normal group. After tendon repair, the wound was closed with 3-0 Vicryl suture. The paws were not immobilized or dressed. After three weeks, the joint flexion of the digits was measured. As indicated by the results shown in Table 2 below, the tendon wrap unexpectedly helped minimize adhesion between the injured tendon and the surrounding tissues.

TABLE 2

|  | Group 2 (n = 6) | Group 1 (n = 7) | Group 3 (n = 7) |
| --- | --- | --- | --- |
| Proximal interphalangeal Joint | 6.5° ± 1.64° | 12° ± 2.52° | 11.17° ± 4.40° |
| Metacarpophalangeal Joint | 11.0° ± 1.94° | 18.17° ± 4.96° | 23.5° ± 11.13° |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A membrane for wrapping around and protecting a cylindrical tissue having an injury site, the membrane comprising:
   a sheet of a porous matrix formed of cross-linked collagen fibers that are oriented, the sheet being spirally rolled so that at least one portion overlaps another portion of the sheet and, upon absorption of a fluid, the overlapping portions closely adhere to each other so as to prohibit cell penetration,
   wherein the cross-linked collagen fibers are oriented in a circumferential direction around the spiral roll; the sheet is re-rollable, resorbable, semipermeable, and cell-occlusive; and the sheet has a thickness of 0.05 mm to 1 mm, a density of 0.05 g/cm$^3$ to 0.8 g/cm$^3$, a permeability to molecules having molecular weights no greater than $2 \times 10^6$ Daltons, a suture pullout strength of 0.1 kg to 1 kg, a re-roll time of 0.1 second to 5 seconds, and an in vivo resorption time of 2 months to 12 months.

2. The membrane of claim 1, wherein the sheet has a thickness of 0.1 mm to 0.4 mm, a density of 0.2 g/cm$^3$ to 0.8 g/cm$^3$, a height of 2 cm to 5 cm, a length of 0.4 cm to 4 cm, a permeability to molecules having molecular weights no greater than $7 \times 10^4$ Daltons, a suture pullout strength of 0.1 kg to 0.7 kg, a re-roll time of 0.1 second to 1 second, and an in vivo resorption time of 4 months to 9 months.

3. The membrane of claim 2, further comprising a bioactive agent.

4. The membrane of claim 1, further comprising a bioactive agent.

5. The membrane of claim 1, wherein the sheet has a permeability to molecules having molecular weights no greater than $1 \times 10^5$ Daltons.

6. The membrane of claim 1, wherein the dimension of the sheet along the circumferential direction is less than twice the circumference of the tissue having the injury site.

7. The membrane of claim 1, wherein the dimension of the sheet along the longitudinal direction extends at least 0.5 cm beyond each of the ends of the injury site.

8. A method for wrapping around and protecting a cylindrical tissue having an injury site, the method comprising:
   placing the membrane of claim 1 in a fluid to allow the membrane to hydrate;
   unrolling the hydrated membrane with a force; and
   bringing the unrolled membrane within the proximity of the injury site, so that, upon release of the force, the membrane re-rolls and wraps the injury site.

* * * * *